United States Patent [19]
Zimmon

[11] Patent Number: 5,947,926
[45] Date of Patent: *Sep. 7, 1999

[54] APPARATUS AND METHOD FOR THE TREATMENT OF THE GASTROINTESTINAL TRACT

[75] Inventor: David S. Zimmon, Port Washington, N.Y.

[73] Assignee: Zimmon Science Corporation, Port Washington, N.Y.

[*] Notice: This patent is subject to a terminal disclaimer.

[21] Appl. No.: 08/934,248

[22] Filed: Sep. 19, 1997

Related U.S. Application Data

[63] Continuation-in-part of application No. 08/597,224, Feb. 6, 1996, Pat. No. 5,785,684, and application No. 08/559,564, Nov. 16, 1995, abandoned.

[51] Int. Cl.⁶ ............................................. A61M 29/00
[52] U.S. Cl. ................................. 604/96; 604/27
[58] Field of Search ................... 604/27, 28, 29, 604/30, 35, 36, 96, 97, 98, 99, 101; 606/192–195; 128/207.14, 200.26

[56] References Cited

U.S. PATENT DOCUMENTS

| | | |
|---|---|---|
| 386,603 | 7/1888 | Parsons . |
| 946,256 | 1/1910 | McNerthney . |
| 1,487,252 | 3/1924 | Lore . |
| 1,820,076 | 8/1931 | Kowan . |
| 2,180,042 | 11/1939 | Ettinger . |
| 2,394,888 | 2/1946 | Betts . |
| 2,486,405 | 11/1949 | Henderson . |
| 2,602,448 | 7/1952 | McKenna . |
| 2,832,341 | 4/1958 | Stack . |
| 3,046,988 | 7/1962 | Moreau . |
| 3,411,506 | 11/1968 | Velasco . |
| 3,433,214 | 3/1969 | Silverman . |
| 3,910,266 | 10/1975 | Kawase . |
| 4,089,337 | 5/1978 | Kronner ................................ 604/27 |
| 4,112,947 | 9/1978 | Nehring . |
| 4,230,108 | 10/1980 | Young . |
| 4,413,988 | 11/1983 | Handt et al. . |
| 4,465,470 | 8/1984 | Kelman ................................ 604/27 |
| 4,485,805 | 12/1984 | Foster, Jr. . |
| 4,495,948 | 1/1985 | Shapiro . |
| 4,512,338 | 4/1985 | Balko et al. . |
| 4,522,205 | 6/1985 | Taylor et al. . |
| 4,525,156 | 6/1985 | Benusa et al. . |

(List continued on next page.)

FOREIGN PATENT DOCUMENTS

| | | |
|---|---|---|
| 0-335 814 A2 | 4/1989 | European Pat. Off. . |
| PCT/GB87/ 00522 | 7/1987 | WIPO . |

*Primary Examiner*—John G. Weiss
*Assistant Examiner*—David J. Cho
*Attorney, Agent, or Firm*—Woodard, Emhardt, Naughton, Moriarty & McNett Patent and Trademark Attorneys

[57] ABSTRACT

A method and apparatus for the treatment of the gastrointestinal tract. In one form of the present invention an irrigation tube is positioned through the patient's mouth, esophagus and into the stomach. An inflatable balloon tamponade device is initially positioned around the external surface of the irrigation tube for delivery within the patient. A pushing member is utilized to move the balloon tamponade device along the outer surface of irrigation tube and into a location adjacent internal bleeding sites. The invention facilitates irrigation and aspiration of the stomach through the irrigation tube by selectively coupling an irrigation fluid reservoir and a fluid recovery reservoir. The irrigation and aspiration is conducted through a substantially closed system to accurately determine fluids present and limit health care staff exposure to bodily fluids.

18 Claims, 8 Drawing Sheets

U.S. PATENT DOCUMENTS

| | | |
|---|---|---|
| 4,752,286 | 6/1988 | Okada . |
| 4,773,430 | 9/1988 | Porath . |
| 4,795,430 | 1/1989 | Quinn et al. . |
| 4,861,333 | 8/1989 | Meador . |
| 5,002,528 | 3/1991 | Palestrant . |
| 5,067,497 | 11/1991 | Greear et al. . |
| 5,190,534 | 3/1993 | Kendell . |
| 5,308,326 | 5/1994 | Zimmon . |
| 5,400,770 | 3/1995 | Nakao et al. ............................... 604/96 |
| 5,509,408 | 4/1996 | Kurtis ....................................... 607/27 |
| 5,512,045 | 4/1996 | Gurchumelidze . |
| 5,792,098 | 8/1998 | Felix et al. ............................... 604/27 |
| 5,836,907 | 11/1998 | Campbell ................................. 604/27 |

APPARATUS AND METHOD FOR THE TREATMENT OF THE GASTROINTESTINAL TRACT

The present application is a continuation-in-part of U.S. patent application Ser. No. 08/597,224, filed Feb. 6, 1996, now U.S. Pat. No. 5,785,684, and U.S. patent application Ser. No. 08/559,564, filed Nov. 16, 1995, now abondoned.

BACKGROUND OF THE INVENTION

The present invention relates generally to the therapeutic treatment of the gastrointestinal tract in a patient having gastrointestinal bleeding. More particularly, one embodiment of the present invention relates to a flexible irrigation tube for deploying a balloon tamponade device in the gastrointestinal tract. Further, the present invention relates to irrigation and aspiration of the stomach. While the present invention was developed for use in treating bleeding sites within the gastrointestinal tract, it may have uses in treating other ailments of the gastrointestinal tract as well as in other areas of medicine.

Often it is necessary to treat bleeding sites within the distal esophagus and proximal stomach, particularly to control bleeding from esophagastric varices. Patients experiencing bleeding esophageal varices are a-it a great risk for exsanguination and the serious complications of aspiration of blood and other gastric contents into the lungs. Therefore, diagnostic and treatment measures must be undertaken immediately to accurately identify the cause of bleeding and limit further bleeding to prevent patient death. In these circumstances, it is traditional and useful to aspirate the stomach of a patient with gastrointestinal bleeding prior to the practitioner performing any diagnostic or therapeutic procedures. This procedure is done to evaluate the magnitude and rate of bleeding and to reduce the risk of pulmonary aspiration by emptying the patient's stomach prior to a diagnostic or therapeutic endoscopic procedure. Currently, the available apparatus for aspirating the stomach utilizes a tube, syringe or aspiration bulb, and a basin filed with water. The patient's stomach is irrigated using the syringe and then emptied with the bloody returns from the stomach often being mixed with the irrigation fluid. Mixing of the bloody returns and the irrigation fluid results from the inevitable fluid carry over from the syringe. This prior technique is inefficient and dirty, and requires that the bloody gastric aspirate be transported and emptied into an adjacent basin or sink.

A common limitation of the prior technique is the spreading of blood and irrigation fluid on the operating room floor, the patient, and the personnel involved in the surgical procedure. Exposure of personnel to a patient's blood constitutes a serious risk for the transmission of diseases, such as AIDS or hepatitis, particularly hepatitis A, B, and C. Exacerbating the spread of blood and irrigating fluid throughout the operating room is the fact that these procedures are often required to be performed in great haste because the patient is actively bleeding.

Another limitation associated with the prior therapeutic technique is the general difficulty in controlling the volume of irrigation fluid used, and to account for the volume of bloody returns. Mixing of fluid inhibits an accurate determination of the volume of irrigation fluid ingested or removed. As a consequence, the patient may receive an excess amount of irrigation fluid that passes from the stomach into the intestine and is then absorbed. Similarly, the volume of blood in the bloody returns cannot be measured quantitatively and in a patient with active bleeding can be a number of liters.

Normally, aspiration of the patient's stomach is performed by passing an oral or nasal gastric tube into the stomach, aspirating the contents which are then examined by the practitioner for the presence of blood, and if blood is present the stomach is irrigated and emptied in preparation for a diagnostic or a therapeutic endoscopic procedure.

Such an endoscopic examination requires the use of expensive sophisticated equipment under the direction of a physician trained in endoscopy techniques. Current therapeutic techniques necessitates that prior to performing an endoscopic examination the oral and/or nasal tube utilized for irrigation and aspiration must be removed and the endoscope passed into the stomach. Subsequently, or as part of the examination, the practitioner may attempt to control the bleeding by one of the many therapeutic techniques that are available including: injection of the bleeding site; thermal methods that coagulate the bleeding site; banding, which is the placement of rubber bands around the bleeding site to produce clot formation and stop the bleeding; or the use of a balloon tamponade device. Currently, the deployment of a tamponade balloon to stop variceal bleeding involves backloading the tamponade balloon on the endoscope prior to passage of the tamponade balloon into the patient over the endoscope.

A limitation common to prior therapeutic techniques utilizing endoscopic treatment is the necessity of having a practitioner trained in endoscopy available. Presently, absent the services of a practitioner trained in endoscopy, the deployment of the balloon tamponade device is not a treatment alternative. Therefore, there are life threatening situations where the patient can not receive treatment with the balloon tamponade device to control bleeding from the esophageal varices for lack of either a medical facility and/or a trained practitioner. The absence of the therapeutic technique and/or the passage of time may compound and complicate the patient's medical condition, particularly where the patent is experiencing massive variceal bleeding and is in danger of exsanguination.

Another limitation associated with the prior therapeutic techniques is the inability to perform irrigation and aspiration while the balloon tamponade device is being deployed. As a result, blood from the actively bleeding injury inhibits the practitioner's ability to visualize the bleeding site with an endoscope and properly diagnose the ailment. Even if the endoscope includes a passage for suction, this small bore passage, often on the order of 3 mm in diameter, is not suited for the removal of large blood clots and the large volume of blood associated with active bleeding of esophageal varices.

A further limitation associated with the prior therapeutic techniques of passing the tamponade device over the endoscope relates to the complex structure of the endoscope. Specifically, an endoscope often includes a complicated operating handle, an umbilical connection to a light source, a video connection, and connection to a suction apparatus. The physical constructs of the endoscope often render the apparatus cumbersome, and requires specialized staff, such as an anesthesiologist, and equipment for tamponade balloon passage not readily available outside of a sophisticated medical treatment facility. Moreover, because of the number of attachments to the endoscope, a treatment device must be back loaded on the endoscope prior to insertion into the patient. This limitation often requires that the endoscope be inserted for diagnosis and then withdrawn to be fitted with a treatment device before being reinserted. Withdrawal and reinsertion of the endoscope prior to treatment of the bleeding site unduly complicates the procedure and expends valuable time in delivering life saving treatment.

Although the prior techniques are steps in the right direction for the treatment of esophagastric variceal bleeding, the need for improvement still remains. The present invention satisfies this need in a novel and unobvious way.

SUMMARY OF THE INVENTION

One form of the present invention contemplates an apparatus for treating a bleeding site within a patient's gastrointestinal tract. The apparatus comprising: an elongated tube configured to be insertable into a gastrointestinal tract; a treatment device disposed on and slidable along an outer surface of the elongated tube, the treatment device for controlling bleeding; and a fluid reservoir selectively coupled to the tube for receiving fluid through the elongated tube.

Another form of the present invention contemplates an apparatus for treating a bleeding site within a gastrointestinal tract. The apparatus comprising: an elongated tube configured to be insertable through an esophagus and into the stomach; a device for treating a bleeding site, the device slidable over an outer surface of the tube; a syringe coupled to the tube; an irrigation fluid delivery reservoir for delivering fluid to the syringe for further delivery to the stomach; and a fluid recovery reservoir for receiving from the syringe at least a portion of the irrigation fluid and other fluids aspirated from the stomach.

Still another form of the invention contemplates a combination for controlling bleeding within a patient. The combination comprising: a hollow elongated flexible member, a portion of the elongated member passable in the oral-gastric tract of a patient; a tamponade device disposed on and slidable along an outer surface of the elongated flexible member, the tamponade adapted to control bleeding in the oral-gastric tract; an irrigation reservoir coupled with the flexible member for delivering fluid through the flexible tube; and a fluid recovery reservoir coupled to the flexible member for receiving fluid through the flexible member.

Another form of the present invention contemplates a method for treating a patient's gastrointestinal tract. The method comprising: providing an elongated tube coupled to a fluid recovery reservoir and a treatment device slidable along the outer surface of the tube; placing the tube into the patient's gastrointestinal tract; aspirating fluid from the patient's gastrointestinal tract through the elongated tube and into the fluid recovery reservoir; and positioning the treatment device adjacent a bleeding site to limit further bleeding.

Yet another form of the present invention contemplates a method for the treatment of a bleeding site within a gastrointestinal tract, The method comprising: providing an elongated tube having a proximal portion adapted for insertion in the gastrointestinal tract and an opposite distal portion, a fluid reservoir, and a treatment device slidable about the elongated tube; placing the elongated tube into the gastrointestinal tract; coupling the elongated tube to the fluid reservoir; establishing a fluid flow through the elongated tube between the gastrointestinal tract and the fluid reservoir; positioning the treatment device about the distal portion of the elongated tube; advancing the treatment device along the elongated tube toward the proximal portion and adjacent an injured site within the gastrointestinal tract; and deploying the treatment device to treat the injured site.

One object of the present invention is to provide an improved apparatus for controlling esophagastric bleeding within a patient.

Still another object of the present invention is to provide an improved apparatus for the irrigation and aspiration of the gastrointestinal tract.

Another object of the present invention is to provide an improved method for deploying a tamponade balloon within a patient.

Yet a further object of the present invention is to provide an improved apparatus for controlling gastrointestinal bleeding, particularly esophagastric variceal bleeding, while permitting simultaneous and continuous irrigation and aspiration of the stomach.

Still another object of the present invention is to provide a simple apparatus that may be quickly and effectively deployed to perform life saving procedures by minimally trained emergency technicians both in hospitals and in remote locations. The device being particularly well suited for field use where patients may expire from gastrointestinal bleeding and its complication before they could be transported to a treatment facility having advanced diagnostic and therapuetic capabilities.

Another object of the present invention is to provide a convenient and efficient method of diagnosing and treating gastrointestinal bleeding without the requirement for advanced medical imaging and endoscopic equipment. The method includes irrigating and aspirating the stomach to diagnosis the patient's condition and inhibit aspiration of blood or gastric contents into the lungs. The irrigation and aspiration may then be continued as a treatment device is advanced over the irrigation tube toward the bleeding site.

Still another object of the present invention is to provide an apparatus and method for diagnosis and treatment of gastrointestinal ailments by insertion of a single tube into the patient. The tube is operable to irrigate and aspirate while simultaneously serving as a guide for deployment of a treatment device.

Related objects and advantages of the present invention will be apparent from the following description.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

The applicant hereby incorporates by reference U.S. application Ser. No. 08/559,564 filed Nov. 16, 1995 and application Ser. No. 08/597,224 filed Feb. 6, 1996. These applications describe an irrigation and aspiration system and a cooperable apparatus for deployment of a balloon tamponade device, respectively.

Figure 1:
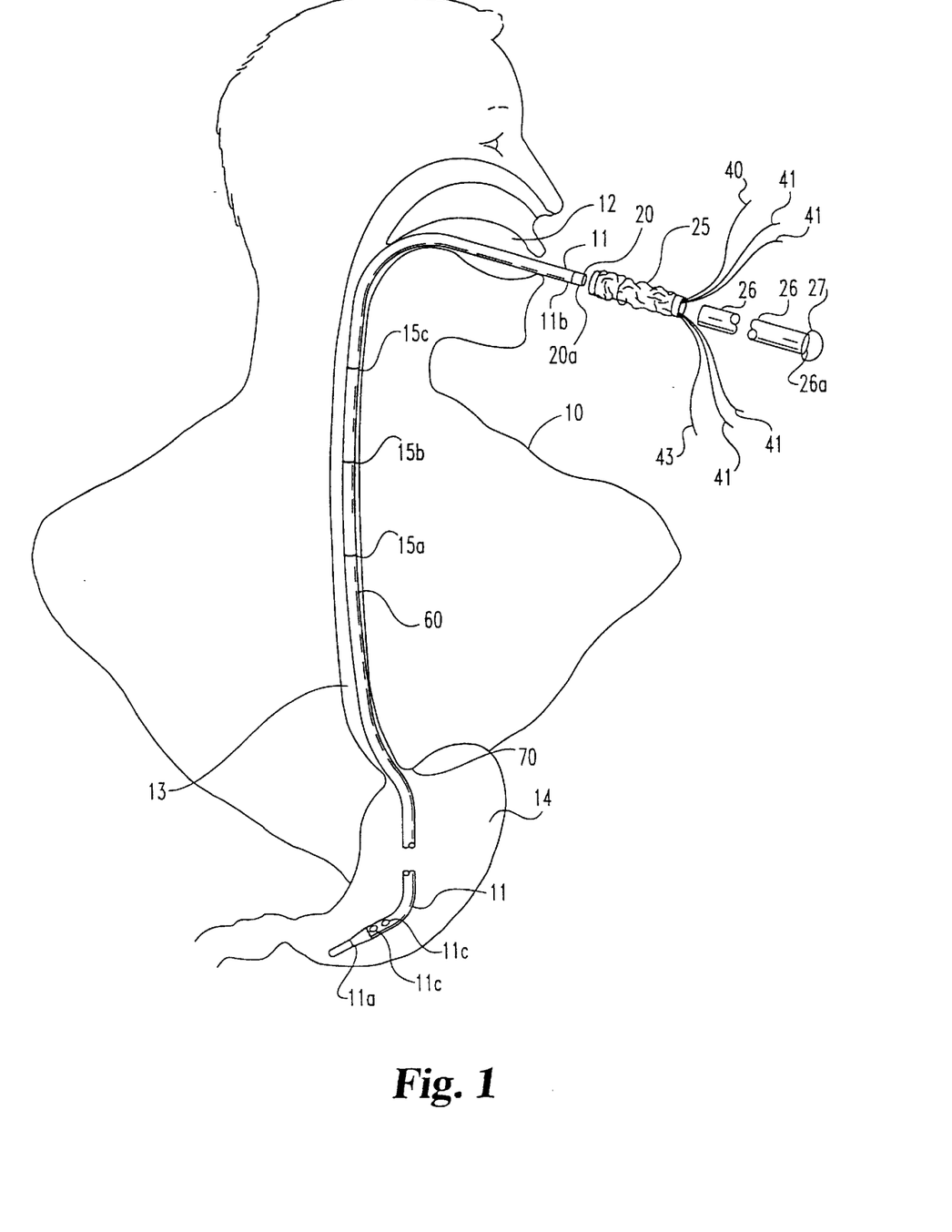
FIG. 1 is a perspective view of a deflated esophagastric balloon tamponade device and irrigation tube according to one form of the present invention.

Referring to FIG. 1 there is shown a perspective view of a portion of the gastrointestinal tract of a patient 10, including the mouth 12, esophagus 13 and stomach 14. A substantially flexible irrigation tube 11 is placed through the patient's mouth 12, esophagus 13, and into stomach 14 to allow irrigation and aspiration of the patient's stomach. Irrigation tube 11 is of sufficient length and diameter such that the contents of the stomach can be irrigated/aspirated by the passage of fluid through the tube 11. In the preferred embodiment the irrigation tube 11 has a length of about 120 centimeters (47.25 inches). The irrigation tube 11 is formed of a material that is compatible with human tissue; and in the preferred embodiment is formed of polyvinyl chloride (PVC). The preferred embodiment of irrigation tube 11 has an outside diameter of about 32 fr (10.7 mm). It is understood that other lengths and diameters are within the contemplation of the present invention provided that they provide the desired characteristics.

Irrigation tube 11 includes a proximal end 11a, that is positionable within stomach 14, and a distal end 11b, disposed at the opposite other end of the tube. In the preferred embodiment the proximal end 11a of irrigation tube 11 includes a plurality of apertures therein for receiving gastric contents of the patient therethrough. In one form of the present invention a pair of spaced apertures 11c are formed along the last 10 centimeters of the tube 11. It is understood that other quantities of apertures on the proximal end are within the contemplation of those skilled in the art. A plurality of insertion length indicators are positioned on the exterior surface 60 of the irrigation tube 11. In one form of the present invention the indicators 15a, 15b, and 15c are positioned respectively about 50 centimeters (19.7 inches) from the proximal end 11a, 60 centimeters (23.6 inches) from the proximal end 11a, and 70 centimeters (27.5 inches) from the proximal end 11a of irrigation tube 11. The insertion length indicators 15a, 15b, and 15c assist the practitioner in determining the depth irrigation tube 11 has been introduced within the patient. In the preferred embodiment, the irrigation tube 11 is inserted 60 centimeters (23.6 inches) into the patient thereby leaving approximately 60 centimeters (23.6 inches) of the tube 11 extending outwardly adjacent the patient's mouth 12.

Referring to FIGS. 1 and 3–5, there is illustrated the irrigation tube 11 having an internal obturator 20 disposed therethrough. Obturator 20 being slidable and removable from within the irrigation tube 11. In the preferred embodiment obturator 20 passes through an aperture 21 extending the length of the irrigation tube 11. Obturator 20 is designed and constructed to minimize and or prevent kinking of the irrigation tube 11 as it is passed through the oral cavity, the esophagus 13 and into the stomach 14. Preferably, upon completion of the passing of irrigation tube 11 within the gastrointestinal tract the obturator 20 is withdrawn. Withdrawal of the obturator 20 is accomplished by grasping end 20a and slowly moving the obturator 20 outwardly relative to tube 11. Upon the removal of obturator 20 there is a fluid communication pathway defined by aperture 21 extending through irrigation tube 11. This passage permits transfer of fluids into and out of the stomach 14 through aperture 21. Prudent medical practice often necessitates that the contents of the patient's stomach be aspirated to obtain a sample of the gastric fluid in order to examine for the presence of blood.

Figure 5:
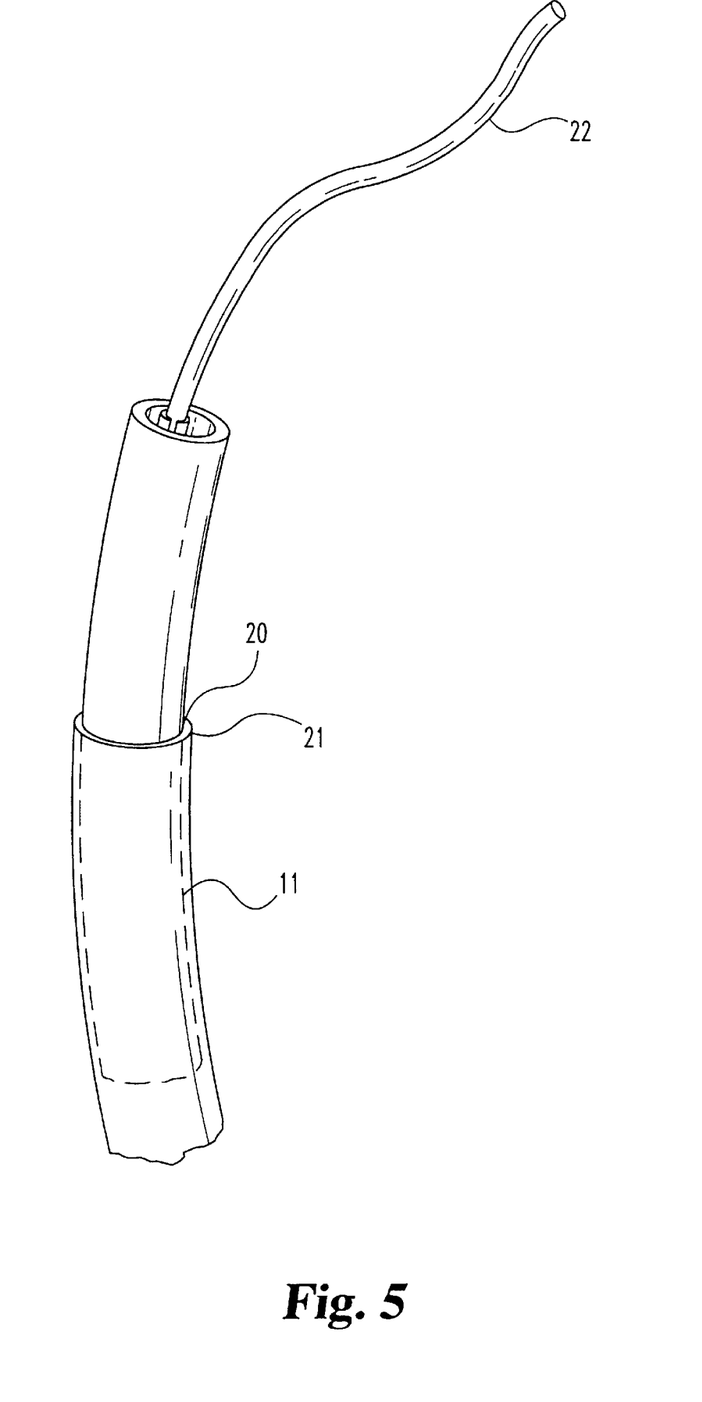
FIG. 5 is a enlarged view of the FIG. 4 irrigation tube with an obturator and wire guide therein.

Further, a wire guide 22 passes through the obturator 20 to facilitate passing the irrigation tube 11 under fluroscopic control. The use of fluroscopic techniques to pass a tube are generally known to those skilled in the art. However, the obturator and tube can be inserted without use of fluroscopic technology, particularly in emergency situations where advanced medical facilities are not available. It is understood by those skilled in the art that the obturator 20 can be tubular, solid, and with or without a wire guide. Variations of the obturator 20 from the preferred embodiment are within the contemplation of the present invention so long as they provide the essential characteristics needed therein.

A balloon tamponade device 25 is designed and manufactured for deployment over the irrigation tube 11 in order to facilitate delivery within the patient. In FIG. 1 the balloon tamponade device 25 is shown in a uninflated condition that is normally used to introduce the balloon within the patient. A pushing member 26 is utilized to advance the uninflated balloon tamponade device 25 along the outer surface of the irrigation tube 11 and into the stomach 14. In the preferred embodiment, the pushing member 26 is a substantially cylindrical tube having a length of about 40 centimeters (15.95 inches) and is formed of polyvinyl chloride. It is understood that pushing member 26 can have other geometric shapes and be formed from a variety of materials. Disposed on an end 26a of the pushing member 26 is a pushing tube controller 27. In the preferred embodiment the pushing tube controller 27 defines a loop or ring designed for grasping by the practitioner. Further, pushing member 26 may have a longitudinal slit extending substantially the entire length thereof to permit placement over the irrigation tube 11 while its distal end 11b is connected to other components. This is particularly useful for maintaining the connection to the irrigation and aspiration system for continuous operation.

Figure 1A:
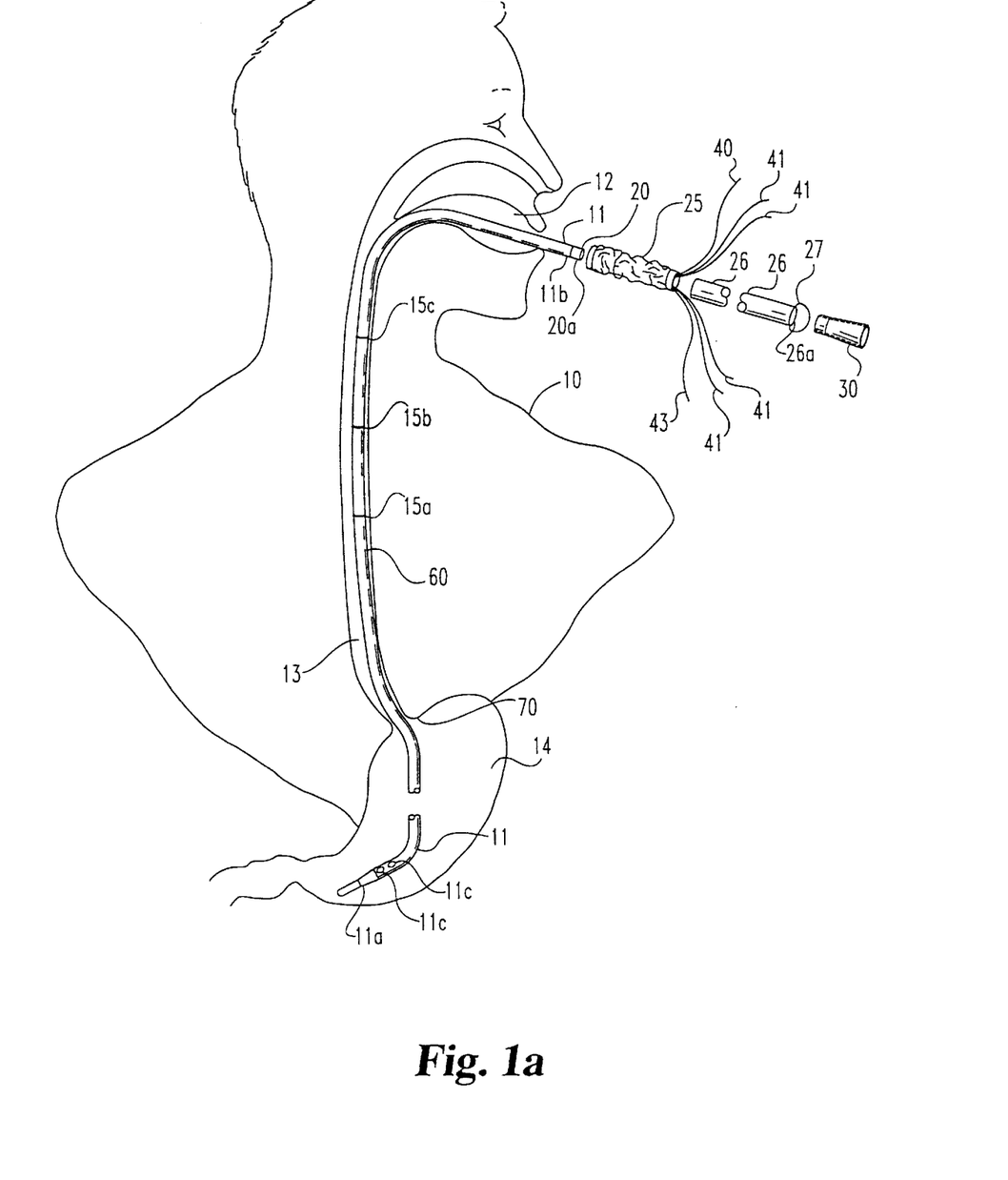
FIG. 1a is a perspective view of a deflated esophagastric balloon tamponade device and irrigation tube according to another form of the present invention.

Referring to FIG. 1a, there is illustrated another form of the present invention. The apparatus illustrated in FIG. 1a is substantially identical to the apparatus set forth in FIG. 1 with the exception that a fluid connecting adaptor 30 has been introduced in FIG. 1a. Fluid connecting adaptor 30 is removable from the irrigation tube 11 and allows for the balloon tamponade device 25 to be loaded on the tube while the proximal end 11a is positioned within the patent. The irrigation tube 11 may then be re-connected to the adapter 30 and the other end of adapter 30 may be connected to an external fluid or suction source. This adapter facilitates the introduction of fluid or suction lo the irrigation tube 11 by an external suction or fluid device. More particularly, fluid connecting adaptor 30 is of a conical shape to allow the coupling of two separate tubes. Further, individuals having ordinary skill in the art will appreciate that there are other types of adapters available to connect two tubes in fluid communication.

Figure 2:
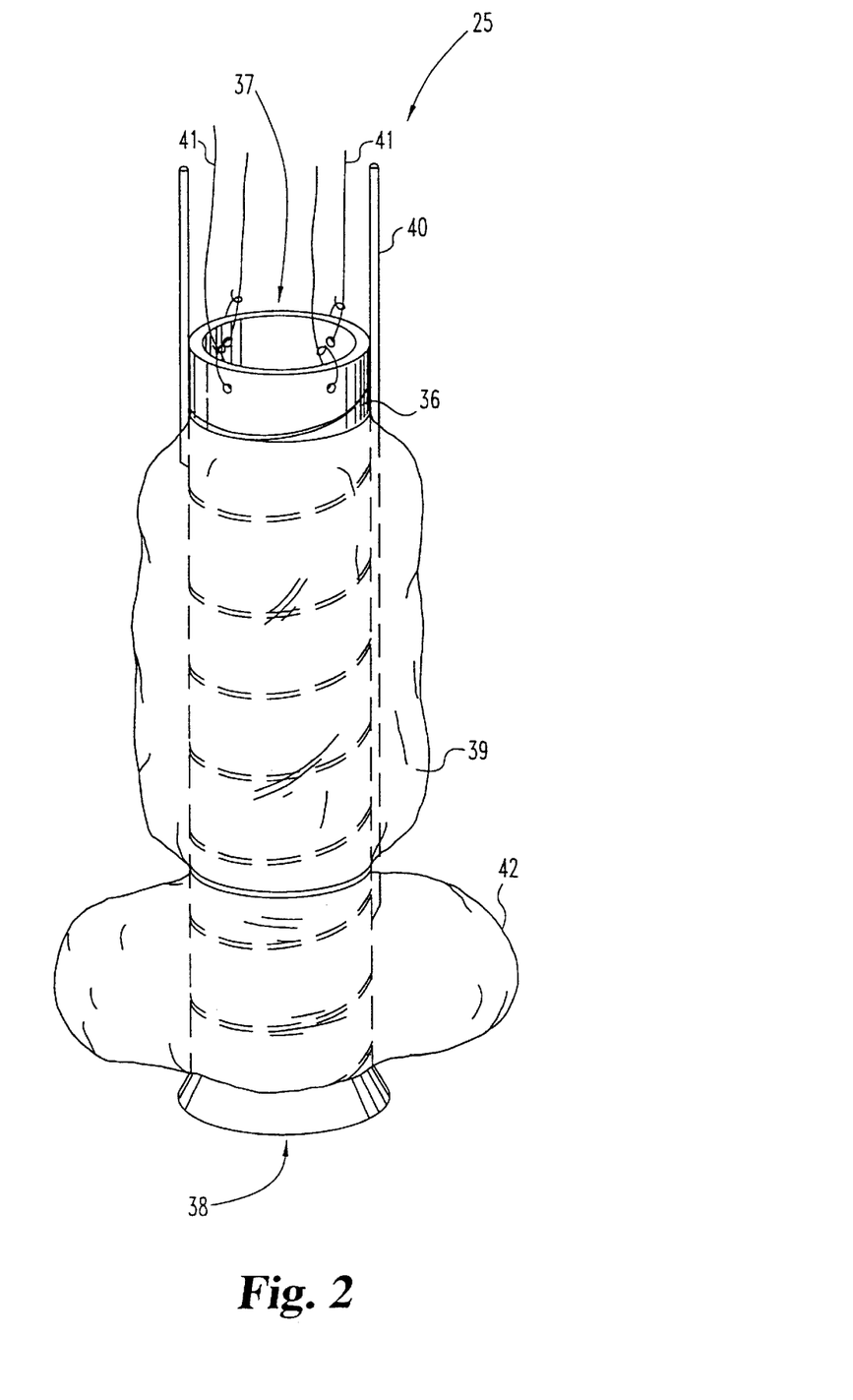
FIG. 2 is a perspective view of the balloon tamponade device comprising a portion of FIG. 1.

Referring to FIG. 2, there is illustrated a perspective view of the preferred embodiment of balloon tamponade device 25. However, it is contemplated that there are other expandable tamponade devices that can pass over and along the irrigation tube 11 and assist in controlling internal bleeding. The Applicant incorporates herein by reference U.S. Pat. No. 5,308,326 describing a Balloon Tamponade Device and Methods for Their Placement. The balloon tamponade device 25 includes a tube 36, a proximal open end 37 and a distal open end 38. An inflatable esophageal balloon 39 is mounted over the tube 36 and an inflation tube 40 is provided for directing pressurized fluid to inflate the esophageal balloon 39.

Wires 41 are attached to the tube 36 and generally form a bridal for securing the balloon tamponade device 25 to a traction instrument (not illustrated). In one form of the present invention the wires 41 extend up the esophagus 13 thereby allowing the device 25 to be secured in place while the proximal open end 37 of the tube 36 is positioned within the esophagus 13. A gastric balloon 42 is mounted over the tube 36 and is adapted to seat against the gastric cardia 70 when inflated in the stomach 14 and thereafter the balloon tamponade device 25 is drawn upward by the wires 41. A second separate inflation lumen 43 is provided to inflate the gastric balloon 42. The inflation lumens 40 and 43 being connectable to external fluid pressurizing sources (not illustrated). Further, details regarding the preferred balloon tamponade device are disclosed in U.S. Pat. No. 5,308,326 which has been incorporated herein by reference. It is understood that other balloon tamponades or treatment devices .or controlling bleeding can be utilized with the present invention.

Although the preferred embodiment utilizes a balloon tamponade device to treat the bleeding location, it is contemplated that other expandable devices or treatment means may be used in conjunction with the components of the present system. These devices should include at least the ability to be deployed while the irrigation tube is in place and provide treatment to the patient.

Figure 3:
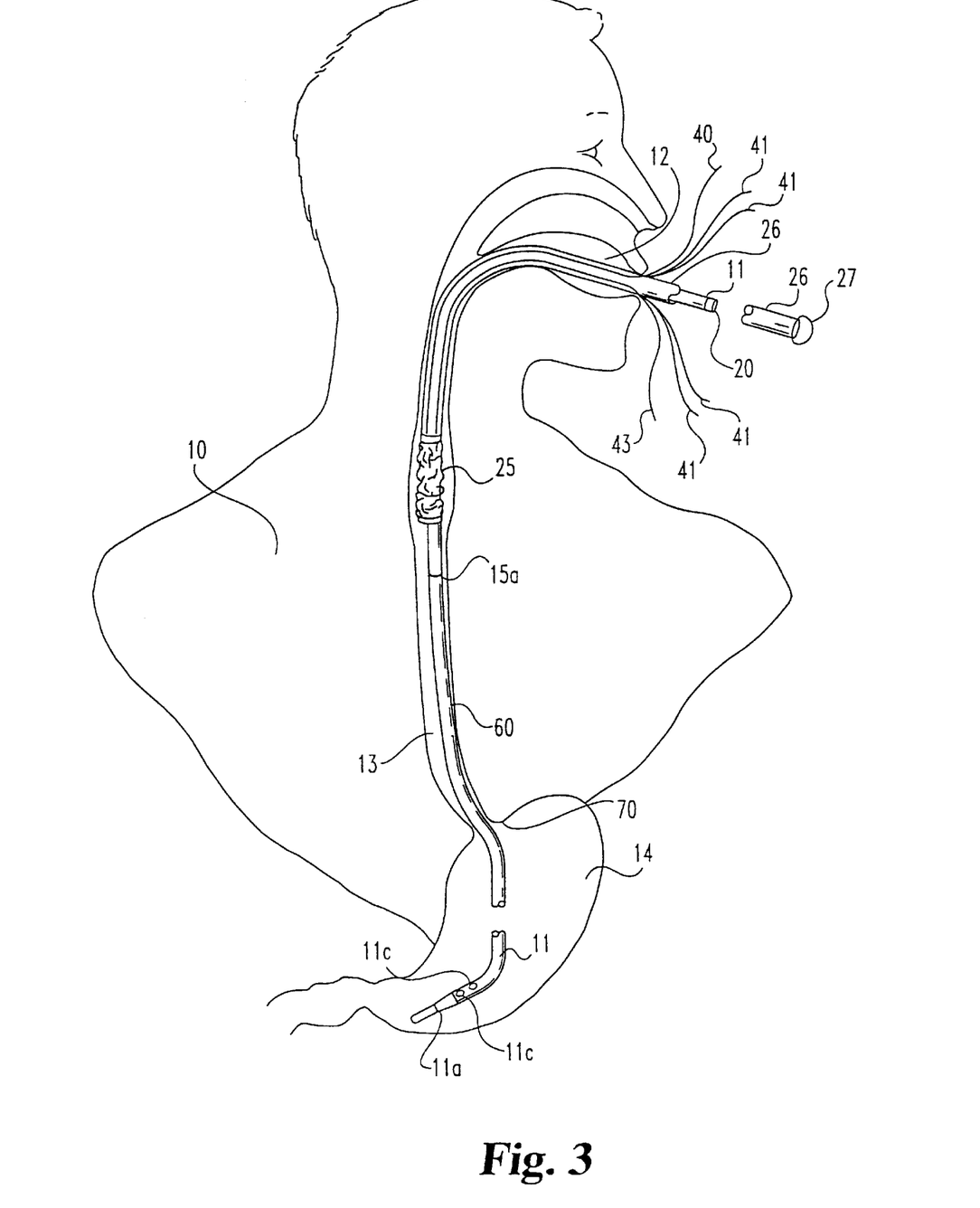
FIG. 3 is a perspective view of FIG. 1 having the balloon tamponade device advanced along the irrigation tube within the FIG. 4 is a perspective view of FIG. 1 having the balloon tamponade device inflated and positioned adjacent the distal end of the esophagus.
Figure 4:
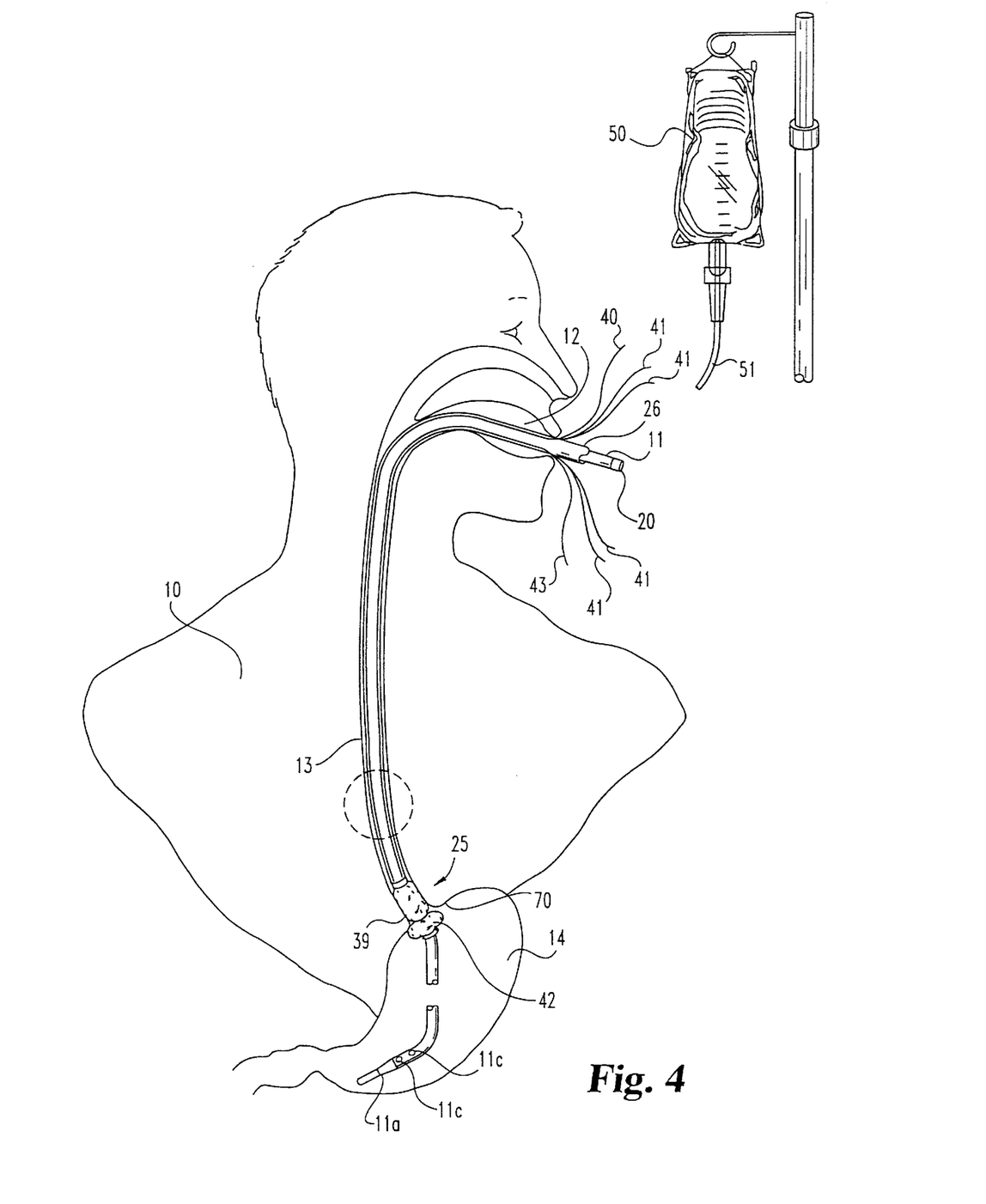

Referring to FIGS. 3 and 4, there is illustrated the balloon tamponade device 25 being positioned along the irrigation tube 11 within the esophagastric system of the patient. It is preferred that the balloon tamponade device 25 be deployed in an uninflated state by placing the balloon tamponade device 25 onto the irrigation tube 11 extending from the patients mouth 12 and then utilizing the pushing member 26 to apply a force sufficient to move the device 25 through the esophagus 13 and into the stomach 14, Pushing member 26 is designed to fit around the outer circumferential surface of the irrigation tube 11 and adjacent the balloon tamponade device 25. The party wishing to deploy the balloon tamponade device 25 must exert a force sufficient to overcome any resistance associated with the esophagus 13 structure and other components. It will be understood by those skilled in the art that the outer surface of the tube or inner surface of the balloon tamponade may include a lubricious coating to decrease resistance when inserting the tube and while advancing the balloon tamponade. Having pushed the balloon tamponade 25 along the outer surface of the irrigation tube 11 it will arrive in the proximal portion of the stomach as illustrated in FIG. 4.

Figure 6:
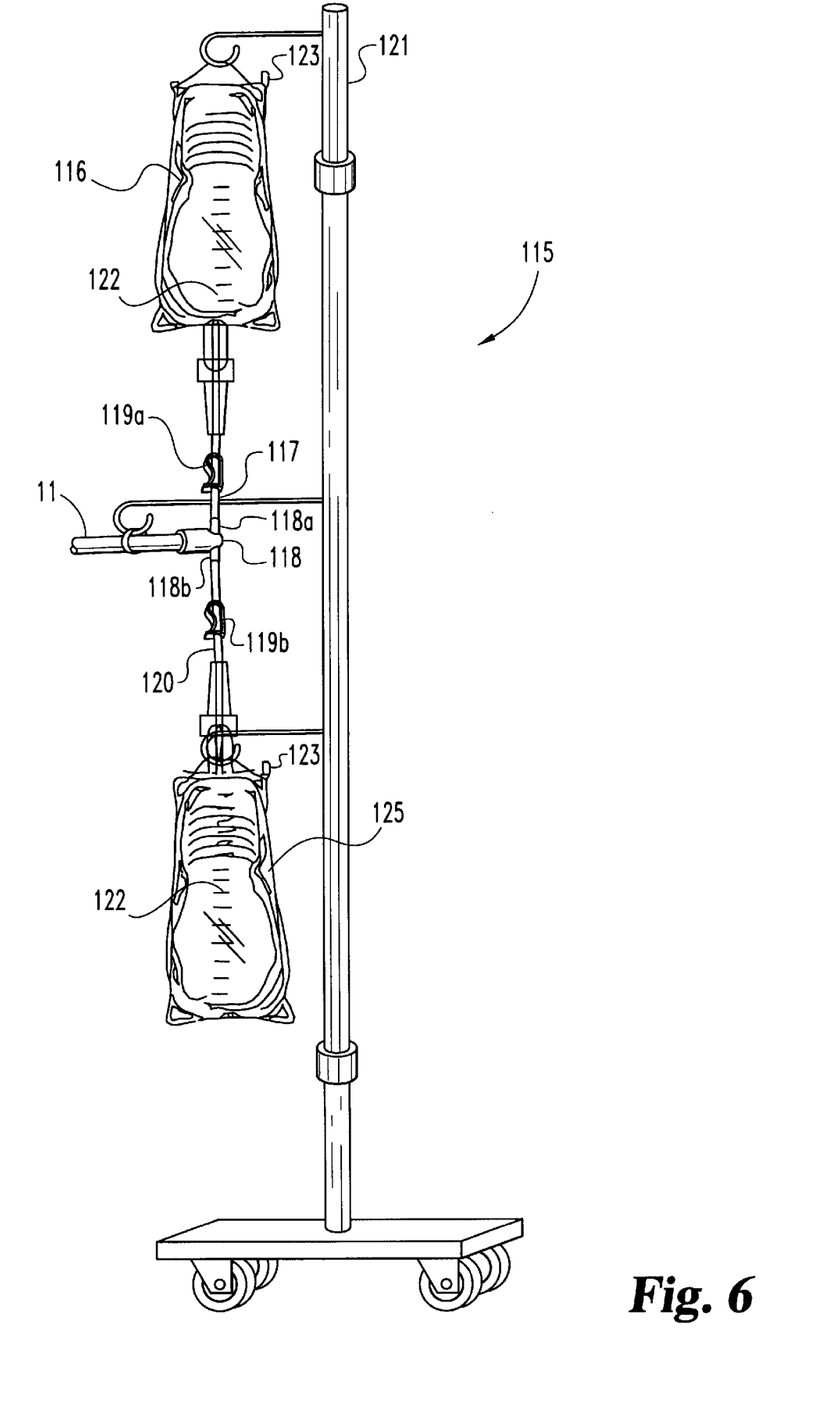
FIG. 6 is a perspective view of an irrigation and aspiration apparatus according to one form of the present invention.
Figure 7:
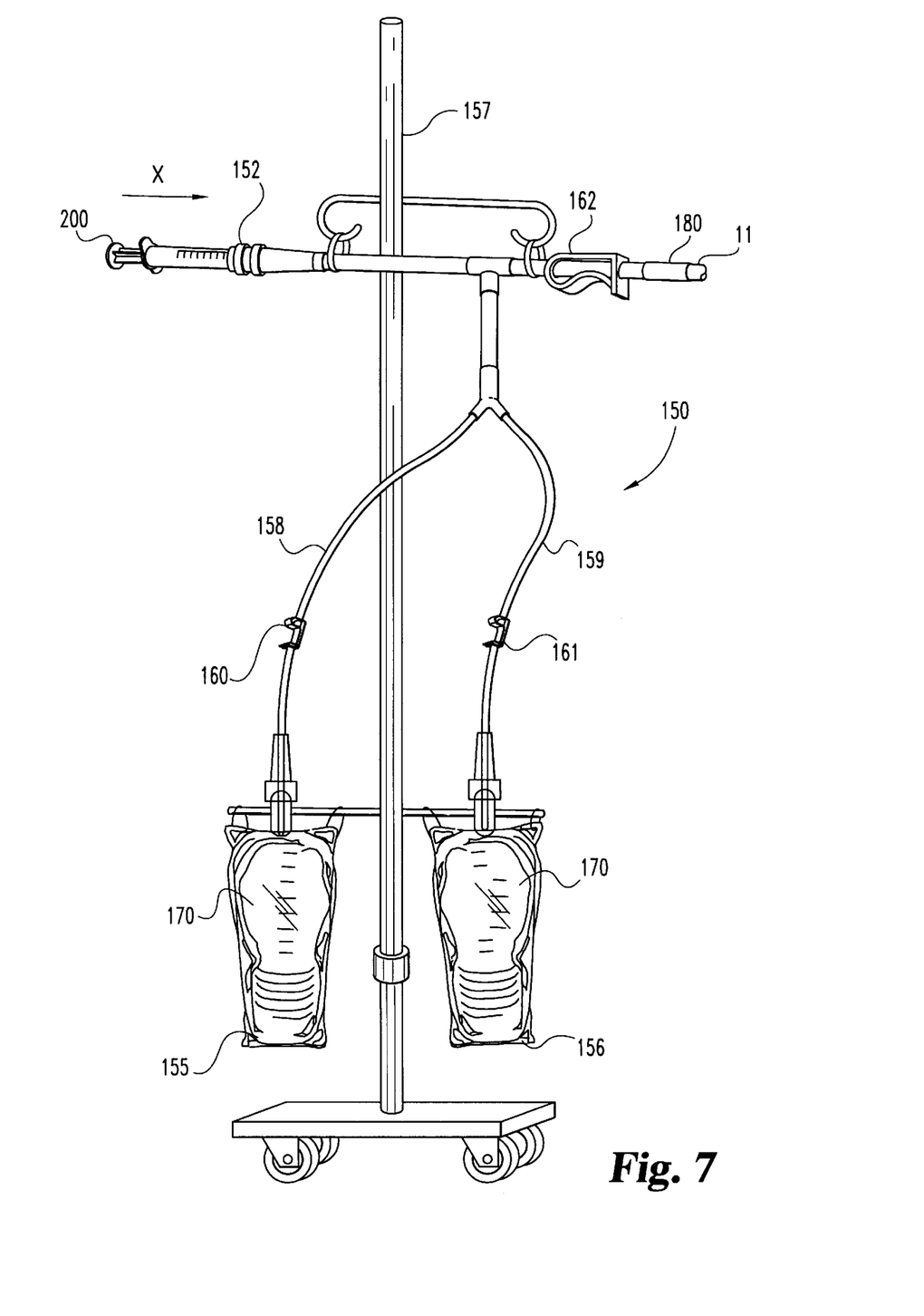
FIG. 7 is a perspective view of an irrigation and aspiration apparatus according to another form of the present invention.

Upon inflating and positioning the gastric balloon 42 and esophageal balloon 39 they function to apply a compressive Force to the distal end of the esophagus 13 and the proximal end of the stomach 14 in order to control bleeding from the esophagastric varices. In the preferred embodiment, the irrigation tube 11 extends 20 centimeters (7.9 inches) within the patient's stomach after the balloon tamponade device has been positioned adjacent the gastric cardia 70. An external fluid reservoir 50 for use in irrigating the stomach 14 is connectable with the irrigation tube 11 to allow the practitioner to irrigate the stomach. Fluid reservoir 50 may also be utilized to hold fluid aspirated from the stomach. Further, a syringe or other aspiration device is connectable to the distal end 11b of irrigation tube 11 in order to aspirate the contents of the stomach. The passage of the irrigation tube 11 allows for the practitioner if necessary to obtain a sample and/or irrigate and aspirate the stomach prior to, during and subsequent to the deployment of the balloon tamponade device 25. Although provided for illustration and without limitation, irrigation and aspiration devices adaptable for use with the irrigation tube and tamponade device are shown in FIGS. 6 and 7. With reference to FIG. 1a there is illustrated one example of a fluid connection adapter 30 that can be utilized to selectively connect the irrigation tube 11 to an irrigation and aspiration system.

With reference to FIG. 6, there is illustrated a preferred embodiment of a closed irrigation-aspiration apparatus 115 for use with the apparatus described above. The apparatus 115 is designed and constructed to provide the efficient and controlled treatment of the stomach 14 of a patient having gastrointestinal bleeding, or one who has ingested a potentially toxic substance. The apparatus 115 is referred to herein as a closed system, and that term means in this context that there are no open connections external to the patient thereby minimizing and/or eliminating the problems associated with blood, irrigation fluid, and other fluids being expelled from the stomach and contaminating the surrounding personnel or facility.

In a preferred embodiment the closed irrigation-aspiration apparatus 115 utilizes two fluid reservoirs that are in fluid communication with the irrigation tube 11. An irrigation fluid reservoir 116 is connected to the irrigation tube 11 by a fluid tubing 117. The fluid tubing 117 being selectively connected to the irrigation tube 11 by a "T"-fitting 118, which has an irrigation fluid side 118a and a fluid return side 118b. Clamps 119a and 119b are configured to be receivable on tubing 117 and tubing 120 respectively to control the flow of fluid through the respective tubes and ultimately the fluid flow into or out of the respective fluid reservoirs. In the preferred embodiment the irrigation fluid is sterile water, which is used to wash a patient's stomach.

Irrigation fluid reservoir 116 is removably connected to a stand 121. The fluid reservoirs, tubes and connectors are all able to be removed and disassembled to facilitate maintenance and the changing of supplies. The stand 121 has an adjustable height to allow a medical practitioner to control the elevation of the irrigation fluid reservoir 116, thereby controlling the force of the fluid flow into the irrigation tube 11, and ultimately to the patient's stomach 14. Stand 121 is merely representative of ways to facilitate elevational changes of the reservoir and should not be viewed as limiting; it is understood that other apparatus providing the same function as stand 121 are contemplated by the present invention. In the preferred embodiment irrigation fluid reservoir 116 is a bag, having a vent 123, with calibration marks 122 formed thereon. It is understood that the reservoir can be a rigid container or a non-rigid container. In the preferred embodiment the calibration marks 122 are positioned at 100 milliliter increments. The calibration marks 122 provide the practitioner with an optical verification as to the quantity of fluid that has been dispensed from the irrigation fluid reservoir 116. A vent 123 is disposed on the top of reservoir 116 to facilitate the flow of fluid from the reservoir.

A fluid recovery reservoir 125 is positioned beneath the irrigation tube 11 in order to facilitate the aspiration of fluid from a patient's stomach by siphonage. It is understood to those skilled in the art that siphonage refers to a method to draw off or empty fluid from a container, such as a stomach by using a siphon. The fluid recovery reservoir 125 is connected to the "T"-fitting 118 by a fluid tube 120 that is connected to the fluid return side 118b. Irrigation tube 11, irrigation fluid reservoir 116, and the fluid recovery reservoir 125 are in a closed fluid communication relationship. Therefore, there are no open connections in the irrigation apparatus 115 external to the patient's stomach. This closed system facilitates the ability to control the volume of irrigation fluid dispensed to the patient's stomach while being able to quantify the amount of irrigation fluid and other fluids aspirated from the patient's stomach.

The closed irrigation-aspiration apparatus 115 has a variety of medicinal applications including the use in patients having active gastrointestinal bleeding and/or patients who have ingested a potentially toxic substance. Upon aspiration of a patient's stomach it is normal to recover a quantity of blood from the bleeding sites, and/or poison from someone who has ingested a potentially toxic substance. Blood and potentially toxic substances will be referred to herein as other fluids, however, this is not intended to be limiting and apparatus 115 is designed and intended for use to aspirate any type of material from the patient's stomach.

With reference to FIG. 7, there is illustrated another embodiment of the irrigation-aspiration apparatus of the present invention. Irrigation-aspiration apparatus 150 is a closed system, as previously defined; and thus there are no open connections external to the patient thereby minimizing or eliminating the contamination of the surrounding environment with blood and/or other fluids. The irrigation-aspiration apparatus 150 includes a pair of fluid reservoirs that are selectively connected to irrigation tube 11 through connector 180. As previously indicated, the irrigation tube 11 includes a portion that is positionable within the patient's gastrointestinal tract and extending into the stomach.

A syringe or bulb aspirator 152 is connected to the irrigation tube 11 to provide the motive power to move the fluids into and out of the patient's stomach. It is preferred that syringe 152 is at least a 100 cc aspiration syringe, and the syringe 152 is utilized to aspirate and irrigate the stomach through the irrigation tube 11. Aspiration syringes and their associated use are generally known to those skilled in the art.

The pair of florid reservoirs include an irrigation fluid reservoir 155 and a fluid recovery reservoir 156 which are adjustably and removably mounted to a stand 157. It is understood that the physical arrangement of the reservoirs 155 and 156 relative to stand 157 can be varied as required by specific local parameters. A pair of tubings 158 and 159 connect their respective fluid reservoirs 155 and 156 to the irrigation tube 11. Each of the tubes 158 and 159 have a clamp 160 and 161 positionable thereon for controlling fluid flow associated with the respective reservoir. The clamps 160 and 161 are identical, and are designed to be manipulated by the practitioner to block the flow of fluid between each reservoir and irrigation tube. A clamp 162 is positionable on irrigation tube 11 in order to control the flow of fluid between apparatus 150 and the patient's stomach. It will be understood by those skilled in the art that while external clamps are shown in the preferred embodiment, a series of valves (one-way, two-way, and/or three-way) could be employed to accomplish the same functions. The important aspect is that the configuration of the apparatus be able to function to irrigate and aspirate the stomach through the irrigation tube.

With reference to FIGS. 1–5 there is illustrated a method of deploying the balloon tamponade device 25 over irrigation tube 11. Irrigation tube 11 and pushing member 26 can be utilized by a physician, a nurse, an emergency technician, and even a trained individual for the deployment of the balloon tamponade device 25. The flexibility in types of people who can deploy the balloon tamponade device without an endoscope allows for use in places remote from physicians offices arid medical emergency rooms. Thus the potentially lifesaving technique of using a balloon tamponade device to prevent bleeding can be utilized in situations that heretofore were not available.

The practitioner/party wishing to introduce the balloon tamponade device 25 begins by passing the irrigation tube 11 into the patient's mouth 12, down the esophagus 13, and into the stomach 14. The length of tube 11 deployed is controllable by the party and generally the tube 11 is placed such that about 60 centimeters (23.6 inches) extend from the patient's mouth 12. The sizing of the tube 11 facilitates placement of the irrigation tube 11 by a non-physician and prepositions the appropriate length of tubing within the stomach 14. An internal obturator 20 may be positioned within the irrigation tube 11 during passage within the patient in order to minimize or eliminate kinking of the tube 11. If so, the obturator 20 is removed and tube 11 is connected to an irrigation and aspiration apparatus the type shown in FIGS. 6 and 7 to permit irrigation and aspiration of the stomach. Aspiration fluid containing blood is a key indicator of internal bleeding. Should internal bleeding be detected, the irrigation and aspiration apparatus may be momentarily disconnected from tube 11 and a balloon tamponade 25 placed over the external surface of irrigation tube 11 extending adjacent the patient's mouth 12. Once tile balloon tamponade is in place, the irrigation/aspiration system may be reconnected to tube 11 to permit continuous irrigation and aspiration during placement of the treatment device. The balloon tamponade 25 is advanced along the tube 11 into position in the patient's stomach 14. In a preferred embodiment, pushing member 26 is slidable over the external surface of tube 11 and adjacent device 25 in order to deliver the necessary force to move the balloon tamponade device 25 to the desired location it is understood that pushing member 26 advances along the irrigation tube 11. In applications where tube 11 is reconnected t o the irrigation/aspiration system, a pushing member 25 with a longitudinal slit can be utilized for ease of operation. Moreover, it is contemplated that the treatment device can be loaded on tube 11 prior to positioning in the patient. With the device pre-loaded, wires within the tube or other connection means can be used to move the treatment device over the tube.

The practitioner/party upon having placed the balloon tamponade device 25 in the proximal end of the stomach, inflates balloon 42, pulls upward on the bridle, and then inflates balloon 39. The inflated balloons 39 and 42 respectively provide sufficient compressive force to treat the bleeding esophageal varices. The guide wires 41 are pulled by the practitioner/party to control movement of the balloon tamponade device 25 within the esophagastric tract, if necessary. If it has not already been withdrawn, obturator 20 is removed from tube 11 and upon its removal aperture 21 is available for the passage of fluid therethrough to irrigate and aspirate the stomach. It is understood that as explained above, obturator 20 is removable prior to the passage of the balloon tamponade device into the patient thereby allowing the practitioner to obtain a sample of the gastric contents or irrigate and aspirate within the patient's stomach before treatment by balloon -tamponade. Further, the practitioner can obtain samples at any other time from the patient's stomach during the medical procedures. It will be understood by those skilled in the art that the continued presence of blood in the aspirated fluid is an indication that the treatment device is not completely stopping the bleeding. In this situation the balloon tamponade may need to be repositioned, balloon pressure increased, or alternative treatment measures undertaken. Once it is determined that the treatment device is properly positioned, tube 11 may be withdrawn from the patient.

An example of one use of irrigation-aspiration apparatus 115 will be set forth to illustrate potential methods of use. The irrigation fluid reservoir 16 is initially filled with a sufficient quantity of irrigation fluid and clamp 119a is positioned on tube 117 to prevent the flow of irrigation fluid from this reservoir to the irrigation tube 11. A second clamp 119b, identical to the first clamp 119a, is clamped across tube 120 to prevent fluid flow into the fluid recovery reservoir 125.

In another form of the present invention, one clamp is utilized to operate this apparatus, and the clamp is moved from tube to tube to open and close the fluid path. After the practitioner has removed clamp 119a from tube 117 and positioned a second clamp 119b on tubing 120 the irrigation fluid can flow from the reservoir 116 through the irrigation tube 11 and into the patient's stomach. It will be understood by one of ordinary skill in the art that the rate and force of the fluid flow is controlled by the vertical adjustment of the irrigation fluid reservoir 116, and the size of the fluid tubing that the fluid flows through. Therefore, prior to allowing the irrigation fluid to flow, the practitioner selects and adjusts the desired elevation for the reservoir 116, and determines the quantity of fluid that should be delivered to the patient. The geometric relationship of the elements of apparatus 115 is associated with providing the motive power necessary to drive the irrigation fluid into the patient's stomach and the operator is free to carefully observe the patient.

The present apparatus 115 alleviates the trauma and irritation that often occurs in prior art manual techniques of this nature, wherein the medical practitioner may inadvertently assert excessive force to an aspiration or irrigation syringe in order to hasten the procedure. In contrast the present invention of apparatus 115 controls the flow of fluids by gravitational forces and differences in pressure. While a preferred embodiment utilizes gravitational forces for fluid delivery and recovery, it is contemplated that a pump could also be used to control fluid flow. However, use of further mechanical devices complicates the procedure and requires additional, unnecessary expense.

After the desired quantity of irrigation fluid has been dispensed from the irrigation fluid reservoir 116 through the irrigation tube 11 into the patient's stomach 14 the practitioner replaces the clamp 119a on the tubing 117 to stop the flow of fluid from this reservoir. The practitioner can now aspirate the stomach 14 by removing clamp 119b that is obstructing the flow of fluid through tube 120. After removal of the clamp 119b from tube 120 the irrigation fluid and other fluids are drawn from the patient's stomach and delivered to the fluid recovery reservoir 125 by a siphon action. Once again the removal of fluid from the stomach is an automated process and does not require manual intervention such as aspiration with a bulb syringe. In order to accomplish the satisfactory treatment of a patient it may be necessary to repeatedly irrigate and aspirate the patient's stomach which may entail adding additional irrigation fluid and additional fluid recovery reservoirs 125. Further, the practitioner can observe the calibration marks 122 on the reservoir 125 to quantify the amount of fluid removed from the stomach.

With reference to FIG. 7, there will now be described an example of the operation of apparatus 150 as deployed for use with an irrigation tube 11. As shown in FIG. 7, the three fluid control clamps 160, 161, and 162 are seated on their respective tubes 158, 159 and 11 to block the flow of fluid therein. A fresh fluid reservoir 155 having a sufficient quantity of irrigation fluid (preferably water) therein is connected to tube 158. It is understood that the tubes and reservoirs are able to be disassembled to facilitate changing the reservoir and maintaining the apparatus. Each of the fluid reservoirs are marked with graduations 170 which facilitate a practitioners recognition of the quantity of fluid delivered from the fluid reservoir 155, and the quantity of fluid drawn from the patient's stomach and delivered into the fluid recovery reservoir 156.

A practitioner inserts the irrigation tube 11 into the patient as illustrated in FIG. 1. The practitioner connects the irrigation-aspiration system 150 to the irrigation tube 11 through connector 180. The clamps 160, 161 and 162 are initially in a closed position. Clamp 162 is opened to allow syringe 152 to be used to aspirate the contents of the stomach. Aspiration is accomplished by applying manual force to the head 200 of the syringe 152 and then releasing. When the fluid retention chamber of syringe 152 is full of fluids aspirated from the stomach, clamp 162 is closed, and then clamp 161 is opened to allow the waste fluid to pass into reservoir 156. The waste florid is expelled from syringe 152 by pushing the head 200 in the direction of arrow X. Following the purging of the syringe 152, clamp 161 is closed and clamp 160 is opened to provide a fluid communication path between irrigation fluid reservoir 155 and syringe 152. Withdrawing the head of the syringe 152 in a direction opposite to arrow X fills the syringe with fresh irrigation fluid. After the syringe 152 is full of a quantity of irrigating fluid the clamp 158 is closed and clamp 162 is opened to create a fluid communication path lo the patient's stomach. Movement of the head 200 in the direction arrow X forces the irrigation fluid through the irrigation tube 11 and into the patient's stomach. The practitioner by varying the amount of force he applies to the head 200 of syringe 152 can adjust the relative force applied to the fluid delivered or drawn from the stomach.

In embodiment 150 of the present invention it is understood that the system is closed and manually aspirated. Further, the calibration marks 170 on fluid reservoir 155 arid 156 allow for a practitioner to visually quantify the amount of irrigation fluid dispensed to the patient, and the amount of irrigation fluid and other fluids aspirated from the patient's stomach. The type of material that is normally aspirated from the patient's stomach includes blood, irrigation fluid, and other ingested materials.

While the invention has been illustrated and described in detail in the drawings and foregoing description, the same is to be considered as illustrative and not restrictive in character, it being understood that only preferred embodiments have been shown and described and that all changes and modifications that cone within the spirit of the invention are desired to be protected.

What is claimed:

1. An apparatus for treating a bleeding site within a gastrointestinal tract, comprising:

an elongated tube configured to be insertable into a gastrointestinal tract;

a treatment device disposed on and slidable along an outer surface of said elongated tube, said treatment device for controlling bleeding;

a means for advancing said treatment device along said elongated tube; and a fluid reservoir selectively coupled to said elongated tube.

2. The apparatus of claim 1, further including an irrigation fluid delivery reservoir comprising an irrigation fluid bag and a delivery tube interconnecting said bag and said elongated tube.

3. The apparatus of claim 1, wherein said fluid reservoir comprises a recovery fluid bag and a recovery tube interconnecting said recovery fluid bag and said elongated tube.

4. The apparatus of claim 3, wherein said recovery bag further comprises calibration marks to determine the volume of fluid recovered.

5. The apparatus of claim 2, wherein said irrigation fluid bag further comprises calibration marks to determine the volume of irrigation fluid delivered.

6. The apparatus of claim 2, wherein said irrigation fluid bag includes a vent for facilitating the flower of fluid from said irrigation fluid bag.

7. The apparatus of claim 1, further comprising a stand, an irrigation fluid delivery reservoir coupled to said stand and having a vertical space associated therewith, said stand being adjustable to adjust said vertical space of said irrigation fluid delivery reservoir to thereby control fluid flow into the gastrointestinal tract.

8. The apparatus of claim 1, wherein said tube is a single lumen tube.

9. The apparatus of claim 1, wherein said means comprises a pusher slidably disposed about at least a portion of said elongated tube.

10. The apparatus of claim 9, wherein said pusher is a tube and includes a longitudinal slot.

11. The apparatus of claim 1, wherein said treatment device is a balloon tamponade device.

12. The apparatus of claim 1, wherein said elongated tube has a proximal portion insertable into a gastrointestinal tract and an opposite distal portion, and said treatment device is slidable over said distal portion and along an outer surface of said tube toward said proximal portion.

13. The apparatus of claim 1, further including an obturator extending through said elongated tube.

14. An apparatus for treating a bleeding site within a gastrointestinal tract, comprising:

an elongated tube configured to be insertable through an esophagus and into the stomach;

means for treating a bleeding site, said means slidable over an outer surface of said tube;

a syringe coupled to said tube;

an irrigation fluid delivery reservoir for delivering fluid to said syringe for further delivery to the stomach; and a fluid recovery reservoir for receiving from said syringe at least a portion of the irrigation fluid and other fluids aspirated frown the stomach.

15. The apparatus of claim 14, further comprising:

a first flow control means for controlling fluid flow through said elongated tube, said first flow control means attached to said elongated tube between the stomach and the connection of both the fluid recovery reservoir and the delivery reservoir;

a fluid delivery tube coupling said fluid delivery reservoir to said elongated tube between said syringe and the stomach;

a second flow control means for controlling fluid flow through said fluid delivery tube, said second flow control means attached to said liquid delivery tube;

a fluid recovery tube coupling said fluid recovery reservoir to said elongated tube between said syringe and the stomach;

a third flow control means for controlling fluid flow through said fluid recovery tube, said third flow control means attached to said fluid recovery tube; and wherein each of said flow control means may be selectively positioned so as to allow said syringe to withdraw irrigation fluid from said irrigation fluid delivery reservoir, to deliver irrigation fluid from said syringe to the stomach, to withdraw fluid from thee stomach and to deposit withdrawn fluid in said fluid recovery reservoir.

16. A combination, comprising:

a hollow elongated flexible member, a portion of said elongated member passable in the oral-gastric tract of a patient;

a treatment device disposed on and slidable along an outer surface of said elongated tube, said treatment device adapted to control bleeding int he oral-gastric tract;

a pushing member positionable adjacent said treatment device for advancing said treatment device alone said flexible member;

an irrigation reservoir coupled with said flexible member for delivering fluid through said flexible tube; and a fluid recovery reservoir coupled to said flexible member.

17. The combination of claim 16, further including an obturator extending through said hollow elongated flexible member.

18. The combination of claim 16, wherein said treatment device is a balloon tamponade device.

* * * * *

UNITED STATES PATENT AND TRADEMARK OFFICE
CERTIFICATE OF CORRECTION

PATENT NO : 5,947,926

DATED : September 7, 1999

INVENTOR(S) : David S. Zimmon

It is certified that error appears in the above-identified patent and that said Letters Patent are hereby corrected as shown below:

In column 1, line 25, please change "a-it" to --at--.
In column 4, line 51, please insert the word --patient-- after the word "the".
In column 6, line 57, please change "lo" to --to--.
In column 7, line 27, please change ".or" to --for--.
In column 9, line 44, please change "florid" to --fluid--.
In column 10, line 7, please change "arid" to --and--.
In column 10, line 31, please change "tile" to --the--.
In column 10, line 40, please change "location it" to --location. It--.
In column 10, line 42, please change "t o." to --to--.
In column 10, line 66, please delete the hyphen, "-" before the word --tamponade--.
In column 12, line 45, please change "arid" to --and--.
In column 13, line 18, please change "flower" to --flow--.
In column 14, line 3, please change "frown" to --from--.
In column 14, line 16, please change "liquid" to --fluid--.
In column 14, line 28, please change "thee" to --the--.
In column 14, line 36, please change "tube" to --flexible member--.
In column 14, line 37, please change "int he" to --in the--.

Signed and Sealed this

Tenth Day of April, 2001

Attest:

NICHOLAS P. GODICI

*Attesting Officer*    *Acting Director of the United States Patent and Trademark Office*